United States Patent
Fright et al.

(10) Patent No.: US 9,179,844 B2
(45) Date of Patent: Nov. 10, 2015

(54) HANDHELD SKIN MEASURING OR MONITORING DEVICE

(71) Applicants: William Richard Fright, Christchurch (NZ); Brent Stephen Robinson, Christchurch (NZ); Shane Robert Goodwin, Christchurch (NZ); Bruce Clinton McCallum, Little River (NZ); Philip John Barclay, Christchurch (NZ)

(72) Inventors: William Richard Fright, Christchurch (NZ); Brent Stephen Robinson, Christchurch (NZ); Shane Robert Goodwin, Christchurch (NZ); Bruce Clinton McCallum, Little River (NZ); Philip John Barclay, Christchurch (NZ)

(73) Assignee: ARANZ HEALTHCARE LIMITED, Christchurch (NZ)

( * ) Notice: Subject to any disclaimer, the term of this patent is extended or adjusted under 35 U.S.C. 154(b) by 0 days.

(21) Appl. No.: 13/686,738

(22) Filed: Nov. 27, 2012

(65) Prior Publication Data
US 2013/0137991 A1 May 30, 2013

Related U.S. Application Data

(60) Provisional application No. 61/564,089, filed on Nov. 28, 2011.

(51) Int. Cl.
*A61B 5/05* (2006.01)
*A61B 5/00* (2006.01)

(52) U.S. Cl.
CPC ............. *A61B 5/0077* (2013.01); *A61B 5/444* (2013.01); *A61B 5/445* (2013.01)

(58) Field of Classification Search
CPC .. A61B 5/0059; A61B 5/0531; A61B 5/0534; A61B 5/1032; A61B 5/442; A61B 5/7257; A61B 5/4547; A61B 5/444; A61B 5/445; G06F 19/345

USPC .......................................................... 382/128
See application file for complete search history.

(56) References Cited

U.S. PATENT DOCUMENTS

| | | |
|---|---|---|
| 4,090,501 A | 5/1978 | Chaitin |
| 4,535,782 A | 8/1985 | Zoltan |
| 4,979,815 A | 12/1990 | Tsikos |
| 5,016,173 A | 5/1991 | Kenet et al. |
| 5,531,520 A | 7/1996 | Grimson et al. |
| 5,561,526 A | 10/1996 | Huber et al. |
| 5,588,428 A | 12/1996 | Smith et al. |
| 5,644,141 A | 7/1997 | Hooker et al. |
| 5,791,346 A | 8/1998 | Craine et al. |

(Continued)

FOREIGN PATENT DOCUMENTS

| | | |
|---|---|---|
| EP | 1248237 | 10/2002 |
| FR | 2570206 | 3/1986 |

(Continued)

OTHER PUBLICATIONS

Ahn, C , et al., "Advances in wound photography and assessment methods", *Adv Skin Wound Care*, 21 (2), (Feb. 2008), 85-93.

(Continued)

*Primary Examiner* — Unsu Jung
*Assistant Examiner* — Joel Lamprecht
(74) *Attorney, Agent, or Firm* — Blakely Sokoloff Taylor & Zafman LLP

(57) ABSTRACT

A handheld skin monitoring or measuring device includes a camera having a camera optical axis; and a structured light arrangement configured to project three or more laser fan beams such that the laser fan beams cross at a crossing point in front of the camera.

18 Claims, 16 Drawing Sheets

(56) References Cited

U.S. PATENT DOCUMENTS

| | | | |
|---|---|---|---|
| 5,946,645 A | 8/1999 | Rioux et al. | |
| 5,957,837 A | 9/1999 | Raab | |
| 5,967,979 A | 10/1999 | Taylor et al. | |
| 5,969,822 A | 10/1999 | Fright et al. | |
| 6,101,408 A | 8/2000 | Craine et al. | |
| 6,215,893 B1 | 4/2001 | Leshem et al. | |
| D453,350 S | 2/2002 | Fenton et al. | |
| D455,166 S | 4/2002 | Raad et al. | |
| 6,381,026 B1 | 4/2002 | Schiff et al. | |
| 6,392,744 B1 | 5/2002 | Holec | |
| 6,413,212 B1 | 7/2002 | Raab | |
| 6,611,617 B1 | 8/2003 | Crampton | |
| 6,678,001 B1 | 1/2004 | Elberbaum | |
| 6,754,370 B1 | 6/2004 | Hall-Holt et al. | |
| 6,873,340 B2 | 3/2005 | Luby | |
| 6,873,716 B1 * | 3/2005 | Bowker et al. | 382/128 |
| D547,347 S | 7/2007 | Kim | |
| D554,682 S | 11/2007 | Martinez et al. | |
| D561,804 S | 2/2008 | Asai et al. | |
| 7,426,319 B2 | 9/2008 | Takahashi | |
| 7,460,250 B2 | 12/2008 | Keightley et al. | |
| 7,474,415 B2 | 1/2009 | Lin et al. | |
| 7,487,063 B2 | 2/2009 | Tubic et al. | |
| D597,205 S | 7/2009 | Koch | |
| D603,441 S | 11/2009 | Wada et al. | |
| 7,724,379 B2 | 5/2010 | Kawasaki et al. | |
| D653,687 S | 2/2012 | Yu | |
| 8,150,500 B2 * | 4/2012 | Goldman et al. | 600/473 |
| 8,755,053 B2 * | 6/2014 | Fright et al. | 356/604 |
| 2003/0231793 A1 | 12/2003 | Crampton | |
| 2004/0059199 A1 | 3/2004 | Thomas et al. | |
| 2004/0136579 A1 | 7/2004 | Gutenev | |
| 2005/0027567 A1 | 2/2005 | Taha | |
| 2005/0084176 A1 | 4/2005 | Talapov et al. | |
| 2006/0044546 A1 | 3/2006 | Lewin et al. | |
| 2006/0210132 A1 | 9/2006 | Christiansen et al. | |
| 2007/0097381 A1 | 5/2007 | Tobiason et al. | |
| 2007/0229850 A1 | 10/2007 | Herber | |
| 2007/0273894 A1 | 11/2007 | Johnson et al. | |
| 2008/0006282 A1 | 1/2008 | Sukovic et al. | |
| 2008/0021329 A1 * | 1/2008 | Wood et al. | 600/476 |
| 2008/0165357 A1 | 7/2008 | Stern | |
| 2008/0232679 A1 | 9/2008 | Hahn et al. | |
| 2008/0246759 A1 | 10/2008 | Summers | |
| 2008/0285056 A1 | 11/2008 | Blayvas | |
| 2009/0213213 A1 | 8/2009 | Fright et al. | |
| 2009/0221874 A1 | 9/2009 | Vinther et al. | |
| 2009/0225333 A1 | 9/2009 | Bendall et al. | |
| 2010/0091104 A1 | 4/2010 | Sprigle et al. | |
| 2010/0149551 A1 | 6/2010 | Malinkevich | |

FOREIGN PATENT DOCUMENTS

| | | |
|---|---|---|
| NZ | 293713 | 9/1997 |
| WO | WO-0030337 | 5/2000 |
| WO | WO-2005033620 | 4/2005 |
| WO | WO-2006078902 | 7/2006 |
| WO | WO-2007029038 | 3/2007 |
| WO | WO-2007043899 | 4/2007 |
| WO | WO-2007059780 | 5/2007 |
| WO | WO-2008033010 | 3/2008 |
| WO | WO-2008039539 | 4/2008 |
| WO | WO-2008048424 | 4/2008 |
| WO | WO-2008057056 | 5/2008 |
| WO | WO-2008071414 | 6/2008 |
| WO | WO-2008080385 | 7/2008 |
| WO | WO-2009046218 | 4/2009 |
| WO | WO-2010048960 | 5/2010 |

OTHER PUBLICATIONS

Ahroni, JH , et al., "Reliability of computerized wound surface are determinations", *Wounds: A Compendium of CLinical Research and Practice*, No. 4, (1992), 133-137.

Armstrong, D G., et al., "Diabetic foot ulcers: prevention, diagnosis and classification", *Am Fam Physician*, 57 (6), (Mar. 15, 1998), 1325-32, 1337-8.

Bale, S , et al., *An Introduction to Wounds*, (2000), 33-40.

Beaumont, E , et al., "RN Technology Scorecard: Wound Care Science at the Crossroads", *American Journal of Nursing*, (12), (Dec. 1998), 16-18, 20-21.

Bergstrom, E , et al., "Treatment of Pressure Ulcers: Clinical Practice Guideline No. 15", *Department of Health and Human Services*, (1994), 95-0652.

Berriss, W P., et al., "Automatic quantitative analysis of healing skin wounds using colour digital image processing", www.worldwidewounds.com, 1997.

Bland, J M., et al., "Measurement error", *BMJ*, 312 (7047) :, (Jun. 29, 1996), 1654.

Bland, J M., et al., "Measurement error and correlation coefficients", *BMJ*, 31 (7048), (Jul. 6, 1996), 41-2.

Bohannon, R W., et al., "Documentation of wound surface area from tracings of wound perimeters", *Physical therapy*, (1983), 1622-1624.

Bolton, L , "Re: Measuring wound length, width, and area: which technique?", *Adv Skin Wound Care*, 21 (10) : 450, (Oct. 2008), Author reply 450-2.

Briers, J D., "Laser speckle contrast imaging for measuring blood flow", *Optica Applicata*, XXXVII (1-2), (2007), 139-152.

Brown, G , "Reporting outcomes for Stage IV pressure uncle healing: a proposal", *Adv Skin Wound Care*, (2000), 13:277-83.

Callieri, M , et al., "Derma: Monitoring the evolution of skin lesions with a 3D system", *8th Internation Fall Workshop, Vision, Modeling, and Visualization*, (Nov. 2003), 167-174.

Campana, et al., "XML-based synchronization of mobile medical devices", *Biomed Tech (Berl)*, 47 Suppl 1Pt, (2002), 2:857-9.

Cardinal, M , et al., "Early healing rates and wound area measurements are reliable predictors of later complete wound closure", *Wound Repair Regen*, 16 (1), (Jan.-Feb. 2008), 19-22.

Cardinal, M , et al., "Wound shape geometry measurements correlate to eventual wound healing", *Wound Repair Regen*, 17 (2), (Mar.-Apr. 2009), 173-8.

Cleator, N , et al.,"Mobile wound care: Transforming care through technology", *Rehab & Community Care Medicine*, (Winter 2008), 14-15.

Collins, C , et al., "The Role of Ultrasound in Lower Extremity Wound Management", *International Journal of Lower Extremity Wounds*, 1, (2002), 229-235.

De Vet, H C., et al., "Current challenges in clinimetrics", *J Clin Epidemiol*, 56 (12), (Dec. 2003), 1137-41.

De Vet, H C., et al., "When to use agreement versus reliability measures", *J Clin Epidemiol*, 59 (10), (Oct. 2006), 1033-9.

Duckworth, M , et al., "A Clinically Affordable Non-Contact Wound Measurement Device", *Proceedings of Rehab Engineering Society of North America (RESNA)*, (2007).

Duff, L , et al., "Guidelines for the management of venous leg ulcers", *Implementation Guide, Royal College of Nursing*, (2000).

Ferrell, B , "Pressure Ulcers. Assessment of healing", *Clin Geriatr Med*, 13, (1997), 575-87.

Fette, A M., "A clinimetric analysis of wound measurement tools", www.worldwidewounds.com, (Jan. 2006).

Fitzpatrick, R , et al., "Evaluating patient-based outcome measures for use in clinical trials", *Health Technol Assess*, 2 (14), (1998), i-iv, 1-74.

Fitzpatrick, R , et al., "Evaluating patient-based outcome measures for use in clinical trials (Executivev Summary)", *Health Technol Assess*, 2 (14), (1998), i-iv.

Flahr, D , et al., "Clinimetrics and wound science", *Wound care Canada*, vol. 3, No. 2, (2005), 18-19, 48.

Flanagan, M , "Improving accuracy of wound measurement in clinical practice", *Ostomy Wound Manage*, 49(10), (Oct. 2003), 28-40.

Flanagan, "Wound measurement: can it help us monitor progression to healing?", *JWound Care*, 12(5), (May 2003), 189-94.

Gethin, G , et al., "Wound measurement: the contribution to practice", *EWMA Journal*, 7 (1), (2007), 26-28.

Gilman, T , "Wound outcomes: the utility of surface measures", *Int J Low Extrem Wounds*, 3 (3), (Sep. 2004), 125-132.

(56) References Cited

OTHER PUBLICATIONS

Goldman, R J., et al., "More than one way to measure a wound: An overview of tools and techniques", *Adv Skin Wound Care*, 15, (2002), 236-45.

Goldman, R J., "The patient.com, 1 year later", *Adv Skin Wound Care*, 15 (6), (Nov.-Dec. 2002), 254, 256.

Griffin, J W., et al., "A comparison of photographic and transparency-based methods for measuring wound surface area", *Phys Ther*, 73 (2), (Feb. 1993), 117-22.

Haghpanah, S , et al., "Reliability of electronic versus manual wound measurement techniques", *Archives of Physical Medicine and Rehabilitation*, vol. 87, Issue 10, (2006), 1396-1402.

Hansen, et al., "Wound status evaluation using color image processing", *IEEE Transactions on Medical Imaging*, vol. 19, No. 1, (1997).

Hayes, S , et al., "Digital photography in wound care", *Nursing Times*, 9(42), (2003), 48-9.

Houghton, p. E., et al., "Photographic assessment of the appearance of chronic pressure and leg ulcers", *Ostomy Wound management*, 46(4), (2000), 20-6, 28-30.

HSA Global, "Mobile Wound Care", *Marketing material*, (2009).

Iakovou, et al., "Integrated sensors for robotic laser welding".

Johnson, J D., "Using ulcer surface area and volume to document wound size", *J Am Podiatr Med Assoc*, 85(2), (Feb. 1995), 91-5.

Jones, T D., et al., "An active contour model for measuring the area of leg ulcers", *IEEE Trans Med Imaging*, 19(12), (Dec. 2000), 1202-10.

Jones, T D., "Improving the Precision of Leg Ulcer Area Measurement with Active Contour Models", *PhD Thesis* http://www.comp.glam.ac.uklpages/staff/tjones/ThesisOL/Title.htm, (1999).

Kecelj-Leskovec, N , et al.,"'Measurement of venous leg ulcers with a laser-based three-dimensional method: comparison to computer planimetry with photography", *Wound Repair Regen*, 15(5), (Sep.-Oct. 2007), 767-71.

Khashram, M , et al., "Effect of TNP on the microbiology of venous leg ulcers: a pilot study", *J Wound Care*, 18(4), (Apr. 2009), 164-7.

Kloth, L C., et al., "A Randomized Controlled Clinical Trial to Evaluate the Effects of Noncontact Normothermic Wound Therapy on Chronic Full-thickness Pressure Ulcers", *Advanced in Skin & Wound Care*, 15(6), (Nov./Dec. 2002), 270-276.

Kober, A , et al., "Three-dimensional documentation of wound healing: first results of a new objective method for measurement", *J Dtsch Dermatol Ges*, 4 (10), (Oct. 2006), 848-54.

Krouskop, T A., et al., "A noncontact wound measurement system", *J Rehabil Res Dev*, 39(3), (May-Jun. 2002), 337-45.

Kudin, J I., et al., "A new way to size up a wound", *American Journal of Nursing*, (2), (1989), 206-7.

Langemo, D K., et al., "Comparison of 2 Wound Volume Measurement Methods", *Advances in Skin & Wound Care*, vol. 14(4), (Jul./Aug. 2001), 190-196.

Langemo, D , et al., "Measuring wound length, width, and area: which technique?", *Adv Skin Wound care*, 21 (1), (Jan. 2008), 42-5.

Langemo, D K., et al., "Two-dimensional wound measurement: comparison of 4 techniques", *Advances in wound Care*, 11(7), (Nov.-Dec. 1998), 337-43.

Laughton, C , et al., "A comparison of four methods of obtaining a negative impression of the foot", *J Am Podiatr Med Assoc*, 92(5), (May 2002), 261-268.

Lewis, P , et al., "Use of store and forward technology for vascular nursing teleconsultation service", *Journal of Vascular Nursing*, 15(4), (1997), 116-123.

Li, D , "Database design and implementation for wound measurement system", *Biophotonics*, (2004), 42-43.

Lorimer, K , "Continuity through best practice: design and implementation for a nurse-led community leg-ulcer service", *Can J Nurs REs*, 36(2), (Jun. 2004), 105-112.

Lowery, J C., et al., "Technical overview of a web-based telemedicine system for wound assessment", *Adv Skin Wound Care*, (4), 2002 165-6, 168-9.

Lowson, S , et al., "The safe practitioner: Getting the record straight: the need for accurate documentation", *Journal of Wound Care*, 13(10), (2004), 1-2.

Lucas, C , et al., "Pressure ulcer surface area measurement using instant full-scale photography and transparency tracings", *Adv Skin Wound Care*, 15(1), (2002), 17-23.

Lunt, M J., "Review of dupTex and colour Doppler imaging of lower-limb arteries and veins", www.worldwidewounds.com, (Sep. 2000).

Maglogiannis, I , et al., "A system for the acquisition of reproducible digital skin lesions images", *Technol Health Care*, 11 (6), (2003), 425-41.

Malian, et al., "MEDPHOS: A new photogrammetric system for medical measurement", *XXth ISPRS Congress: Proceedings of Commission V*, Istanbul, Turkey, (2004), 311-316.

Marjanovic, D , et al., "Measurement of the vol. Of a leg ulcer using a laser scanner", *Physiological Measurement*, 19(4), (1998), 535-43.

Mastronicola, D , et al., "Burn depth assessment using a tri-stimulus colorimeter", *Wounds*, vol. 17, Issue 9, (2005), 255-258.

McArdle, J , et al., "Visitrak: wound measurement as an aid to making treatment decisions", *Diabetic Foot*, 8, (2005), 207-211.

Molnar, J A., et al., "Use of standardized, quantitative digital photography in a multicenter Web-based study", *Eplasty*, (2009), 9:e4.

National Pressure Ulcer Advisory, Panel , "Documentation photography FAQ".

National Pressure Ulcer Advisory, Panel , "The NPUAP Position Statement", http:/lwww.npuap.org/positn5.html, (1998).

Oduncu, H , et al., "Analysis of skin wound images using digital color image processing: a preliminary communication", *Lower Extremity Wounds*, 3(3), (2004), 151-156.

Pages, et al., "Plane to plane positioning from image-based visual servoing and structured lights".

Patete, p. V., et al., "A non-invasive, three-dimensional, diagnostic laser imaging system for accurate wound analysis", *Physiol Meas*, 17(2), (1996), 71-9.

Payne, C , "Cost benefit comparison of plaster casts and optical scans of the foot for the manufacture of foot orthoses", *Australasion Journal of Podiatric Medicine*, 41(2), (2007), 29-31.

Plassmann, P , et al., "MAVIS: a non-invasive instrument to measure area and volume of wounds", *Med Eng Phys*, 20(5), (Jul. 1998), 332-8.

Plassmann, P , "Recording Wounds—Documenting Woundcare", *Powerpoint presentation*, (1998).

Rogers, L C., et al., "Measuring wounds: Which stick to use", *Podiatry Management*, (Aug. 2008), 85-86, 88, 90.

Romanelli, et al., "Technological Advances in Wound Bed Measurements", *Wounds*, 14(2), (2002), 58-66.

Russell, L , "The importance of wound documentation and classification", *British Journal of Nursing*, 8(20), (1999), 1342-1343;1346;1348-1350;1352-1354.

Salcido, R , et al., "Pressure Ulcers and WOund Care", http://www.emedicine.com/pmr/topic179.htm, (2006).

Salcido, R , "The future of wound measurement", *Adv Skin Wound Care*, 13, (2000), 54, 56.

Sani-Kick, S , et al., "Recording and trasmission of digital wound images with the hep of a mobile device", *Biomed Tech (Berl)*, 47 Suppl 1 Pt 2, (2002), 968-969.

Santamaria, N , et al., "The effectiveness of digital imaging and remote expert wound consultation of healing rates in chronic leg ulcers in the Kimberley region of Western Australia", *Primary Intention*, 12(2), (2004), 62-64; 66-68; 70.

Schultz, G S., et al., "Wound bed preparation: a systematic approach to wound management", *Wound Repair Regen*, 11 Suppl 1, (Mar. 2003), S1-28.

Shaw, J , et al., "An evaluation of three wound measurement techniques in diabetic foot wounds", *Diabetic Care*, 30 (10), (Oct. 2007), 2641-2.

Sheehan, P , et al., "Percent change in wound area of diabetic foot ulcers over a 4-week period is a robust predictor of complete healing in a 12-week prospective trial", *Diabetics Care*, 26 (6), (Jun. 2003), 1879-1882.

Smith, et al., "Three-dimensional laser imaging system for measuring wound geometry", *Lasers Surg Med*, 23(2), (1998), 87-93.

Smith & Nephew, "Guidelines for the Management of Leg Ulcers in Ireland", www.smith-nephew.com.

(56) References Cited

OTHER PUBLICATIONS

Smith & Nephew, "Visitrak Wound Measurement Device", www.smith-nephew.com.

Solomon, C, et al., "Use of video image analysis for the measurement of venous ulcers", *Br J Dermatol*, 133(4), (Oct. 1995), 565-570.

Tellez, R, "Managed care making photo documentation a wound care standard", *Wound care solutions product catalogue*, (1997).

Thawer, et al., "A comparison of computer-assisted and manual wound size measurement", *Ost/Wound Manag*, 48(10), (2002), 46-53.

Treuillet, S, et al., "Three-dimensional assessment of skin wounds using a standard digital camera", *IEEE Trans Med Imaging*, 28 (5), (May 2009), 752-762.

Vermolen, F J., et al., "A simplified model for growth factor induced healing of circular wounds", *Reports of the Department of Applied Mathematical Analysis*, Delft University of Technology, Delft Institute of Applied Mathematics, (May 4, 2005).

Wallenstein, S, et al., "Statistical analysis of wound-healing rates for pressure ulcers", *Am J Surg*, 188 (1A Suppl), (Jul. 2004), 73-78.

Wang, Y, et al., "A comparison o digital planimetry and transparency tracing based methods for measuring diabetic cutaneoud ulcer surface area", *Zhongguo Xiu Fu Chong Jian Wai Ke Za Zhi*, 22 (5), (May 2008), 563-566.

Wendelken, M, et al., "Feature: Key Insights on Mapping Wounds With Ultrasound", *Podiatry Today*, 19(7), (2006), 70-74.

Wilbright, W A., et al., "The use of telemedicine in the management of diabetes-related foot ulceration: a pilot study", *Adv Skin Wound Care*, 5 Pt 1, (2004), 232-238.

Wild, T, et al., "Wound healing analysis and measurement by means of colour segmentation", *ETRS POster Presentation V28*, (2008).

Williams, C, "The Verge Videometer wound measurement package", *Br J Nurs*, 9(4), (Feb. 24-Mar. 8, 2000), 237-239.

Woodbury, et al., "Development, validity, reliability, and responsiveness of a new leg ulcer measurement toolq", *Adv Wound Care*, 17, (2004), 187-196.

Woodbury, M G., et al., "Pressur Ulcer Assessment Instruments: a critical appraisal", *Ostomy Wound Management*, 45(5), (1999), 42-45, 48-50, 53-55.

Xiang, L, et al., "Wound measurement by curvature maps: a feasibility study", *Physiol. Meas 27*, (2006), 1107-1123.

Zuijlen, et al., "Reliability and accuracy of techniques for surface area measurements of wounds and scars", *International Journal of Lower Extremity Wounds*, 3(1), (2004), 7-11.

\* cited by examiner

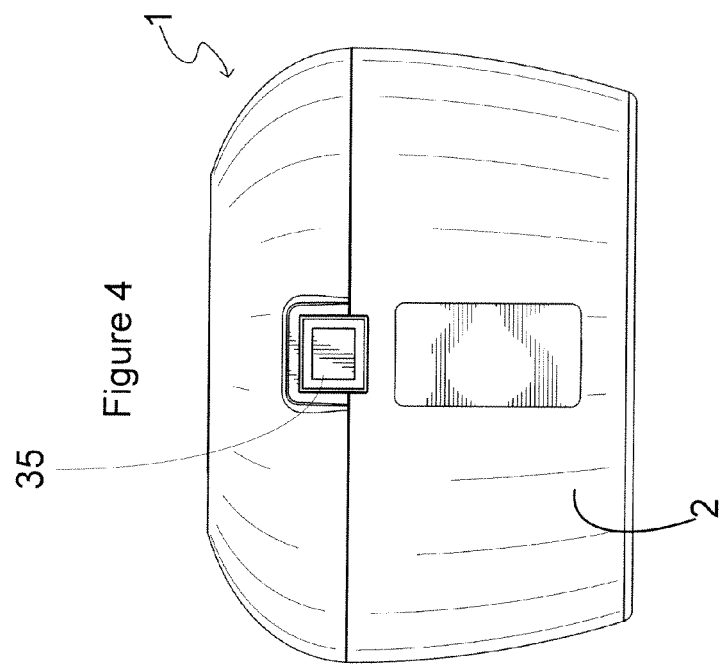
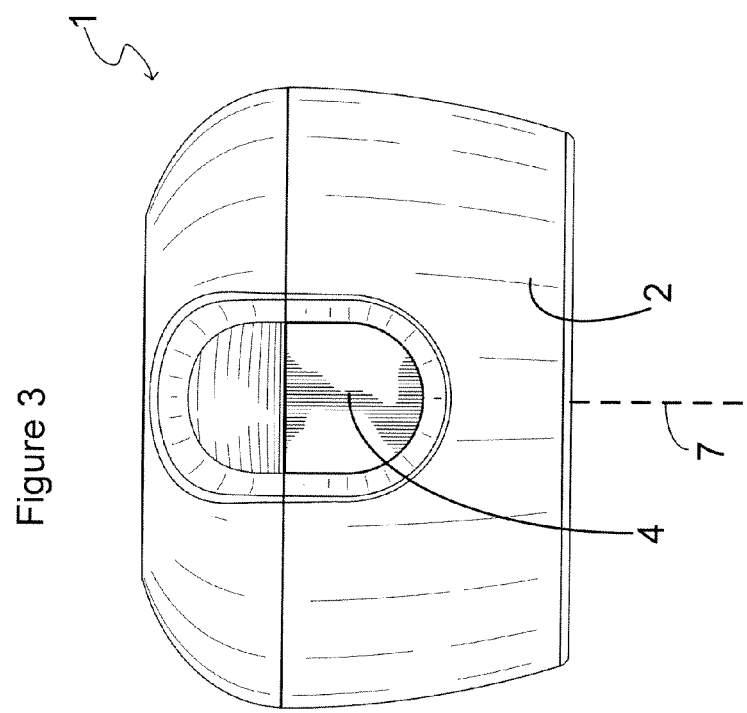

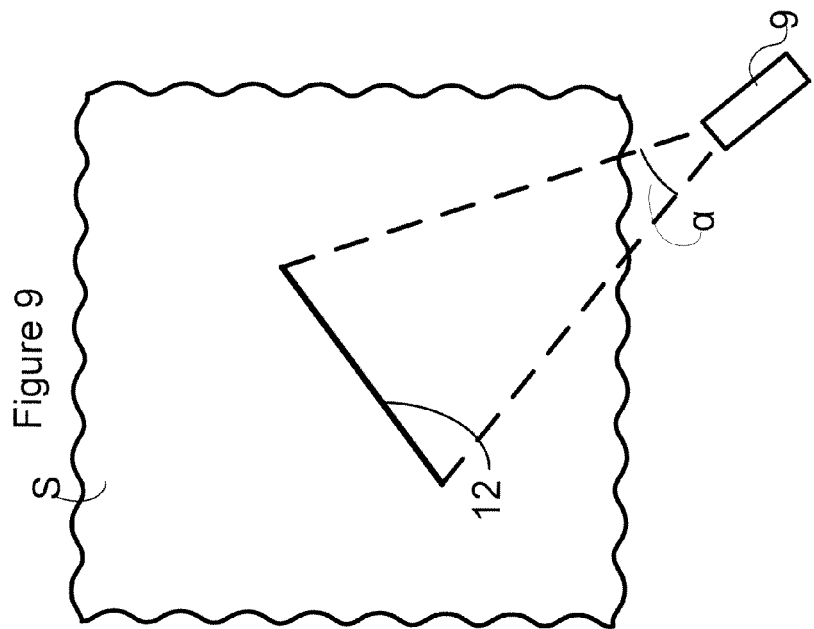
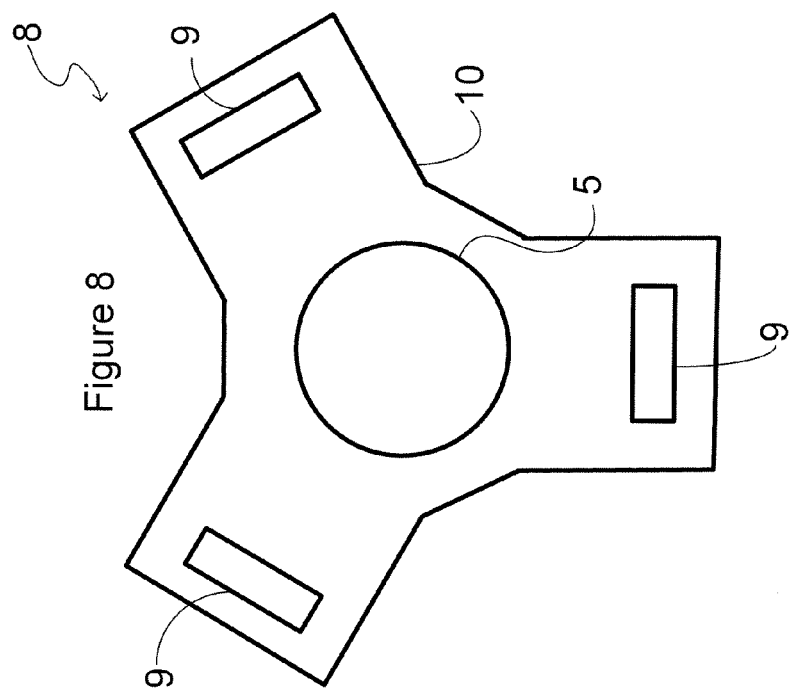

HANDHELD SKIN MEASURING OR MONITORING DEVICE

FIELD OF THE INVENTION

The invention relates to devices and methods for monitoring or measuring skin features, such as wounds, ulcers, sores, lesions, tumors, bruises, burns, psoriasis, keloids, skin cancers, erythema, cellulitis or the like.

BACKGROUND TO THE INVENTION

Reference to any prior art in this specification does not constitute an admission that such prior art forms part of the common general knowledge.

Various techniques have been used to monitor wounds, ulcers, sores, lesions, tumors etc. (herein referred to collectively as "wounds") both within hospitals and outside hospitals (e.g. in domiciliary based care, primary care facilities etc.). Manual techniques are typically labor-intensive and require examination and contact by skilled personnel. Such measurements may be inaccurate and there may be significant variation between measurements made by different personnel. Further, traditional approaches may not preserve any visual record for review by an expert or for subsequent comparison.

A number of techniques for the automated monitoring of wounds have been proposed; see for example U.S. Pat. No. 6,101,408, U.S. Pat. No. 6,873,340, U.S. Pat. No. 4,535,782 and U.S. Pat. No. 5,967,979. A common approach is to place a reference object next to the wound and determine the size of the wound utilizing the scale of the reference object. It is often undesirable to place a reference object near to a wound and this requires an additional cumbersome step for a user and risks contamination of the wound. Further, when the target is not in the plane of the wound, or if the wound is not planar, there will be errors in any area calculation.

Other systems, such as that described in US2004/0136579, require the camera always to be positioned with a guide against the patient's skin. While this consistently positions the camera a desired distance from the surface to be photographed and therefore sets the scale of the image, it is unwieldy and requires undesirable contact with the skin, risking contamination of the wound.

Many prior systems also suffer from high cost, which limits uptake of the systems.

The Applicant's prior specification published as US2009/213213 proposed a handheld surface measuring device based on a structured light device. (The contents of that specification are hereby incorporated by reference herein.) A laser fan-beam was projected at a known angle to a camera optical axis and the resulting image data could be used to measure wound properties such as area or depth. However, the Applicant has recognized that further improvements in wound measurement are possible.

It is an object of the invention to provide an improved device for monitoring or measuring skin features, or to at least provide the public with a useful choice.

SUMMARY OF THE INVENTION

The invention provides a handheld skin monitoring or measuring device, method and system. The invention relies on structured light techniques and in some embodiments uses a structured light arrangement configured to project three or more laser fan beams such that the laser fan beams cross at a crossing point in front of the camera.

In a first aspect the invention provides a handheld skin monitoring or measuring device, including: a camera having a camera optical axis; and a structured light arrangement configured to project three or more laser fan beams such that the laser fan beams cross at a crossing point in front of the camera.

Preferably the structured light arrangement is configured to project the laser fan-beams such that a pattern formed by the laser fan-beams on a skin surface varies with a distance between the device and the skin surface, and wherein the pattern is a predetermined pattern when the device is at a distance from the skin surface within an optimum range, such that a user is enabled to position the handheld skin monitoring or measuring device at a distance from the skin surface within the optimum range by adjusting the distance such that the predetermined laser pattern is formed on the surface.

Preferably the predetermined pattern includes the laser fan-beams crossing at the crossing point, and a user is enabled to position the handheld skin monitoring or measuring device at a distance from a skin surface within an optimum range by aligning the crossing point with the skin surface.

Preferably the camera has a camera field of view and the three or more laser fan beams subtend fan beam angles corresponding to the camera field of view, such that the ends of the laser beams projected onto a skin surface define a region that substantially corresponds to an image frame of the camera.

Preferably the region occupies between 80% and 120% of the area of the image frame.

Preferably the device has no display.

Preferably the device further includes a capture switch, the device being arranged to capture data on actuation of the capture switch.

Preferably the device further includes a communications port, the device being configured to transmit data captured by the camera from the communications port.

Preferably the device further includes memory configured to store data captured by the camera.

Preferably the device further includes one or more light sources configured to illuminate the skin surface.

Preferably the device is configured to capture at least the following data in response to a single user capture instruction: an image with the laser fan beams switched off; and at least three images each including one or more laser fan beams, such that each laser fan beam is unambiguously identifiable.

Preferably the device further includes a substantially spherical housing dimensioned to fit a user's cupped hand, the camera and structured light arrangement being mounted in the housing.

Preferably the structured light arrangement is configured to project three laser fan beams from sources distributed evenly around the camera optical axis such that the three laser fan beams form an equilateral triangle in any plane that is perpendicular to the camera optical axis and does not include the crossing point.

Preferably the structured light arrangement is configured to project three laser fan beams.

In a second aspect the invention provides a handheld skin monitoring or measuring device, including: a camera having a camera optical axis and a camera field of view; and a structured light arrangement configured to project three or more laser fan beams such that the laser fan beams cross at a crossing point in front of the camera, the laser fan beams subtending fan beam angles corresponding to the camera field of view, such that the ends of the laser beams projected onto a skin surface define a region that substantially corresponds to an image frame of the camera.

Preferably a user can position the handheld skin monitoring or measuring device at a distance from a skin surface within an optimum range by adjusting the distance such that a predetermined laser pattern is projected onto the surface.

Preferably a user can position the handheld skin monitoring or measuring device at a distance from a skin surface within an optimum range by aligning the crossing point with the skin surface.

Preferably the region occupies between 80% and 120% of the area of the image frame.

Preferably the device has no display.

Preferably the device further includes a capture switch, the device being arranged to capture data on actuation of the capture switch.

Preferably the device further includes a communications port, the device being configured to transmit data captured by the camera from the communications port.

Preferably the device further includes memory configured to store data captured by the camera.

Preferably the device further includes one or more light sources configured to illuminate the skin surface.

Preferably the device is configured to capture at least the following data in response to a single user capture instruction: an image with the laser fan beams switched off; and at least three images each including one or more laser fan beams, such that each laser fan beam can be unambiguously identified.

Preferably the device further includes a substantially spherical housing dimensioned to fit a user's cupped hand, the camera and structured light arrangement being mounted in the housing.

Preferably the structured light arrangement is configured to project three laser fan beams from sources distributed evenly around the camera optical axis such that the three laser fan beams form an equilateral triangle in any plane that is perpendicular to the camera optical axis and does not include the crossing point.

Preferably the structured light arrangement is configured to project three laser fan beams.

In a further aspect the invention provide a method of capturing data concerning a skin feature using a handheld skin monitoring or measuring device, including: a camera having a camera optical axis and a camera field of view; a structured light arrangement configured to project three or more laser fan beams such that the laser fan beams cross at a crossing point in front of the camera; the laser fan beams subtending fan beam angles corresponding to the camera field of view, such that the laser beams projected onto a skin surface define a region that substantially corresponds to an image frame of the camera; the method including: directing the handheld skin monitoring or measuring device towards a skin surface; projecting at least some of the laser fan beams using the structured light arrangement; and adjusting a position of the handheld skin monitoring or measuring device such that laser fan beams define a desired image region on the skin surface; and capturing data using the camera.

In a further aspect the invention provides a display-less handheld skin monitoring or measuring device including: a substantially spherical housing dimensioned to fit the cupped hand of a user; a camera mounted in the housing; a structured light arrangement mounted in the housing and configured to project three or more laser fan beams such that the laser fan beams cross at a crossing point in front of the camera; and a communications link configured to transmit image data captured by the camera.

BRIEF DESCRIPTION OF THE DRAWINGS

The invention will now be described by way of example only, with reference to the accompanying drawings, in which:

FIG. 3 is a first side view of the device of FIG. 1;

FIG. 4 is a second side view of the device of FIG. 1;

FIG. 8 shows the mounting of the camera and structured light according to one embodiment;

FIG. 9 shows a laser fan-beam projector projecting a laser fan-beam onto a surface;

DETAILED DESCRIPTION OF PREFERRED EMBODIMENTS

The invention relates to devices for monitoring or measuring skin features, such as wounds, ulcers, sores, lesions, tumors, bruises, burns, psoriasis, keloids, skin cancers, erythema, cellulitis or the like.

Figure 6:
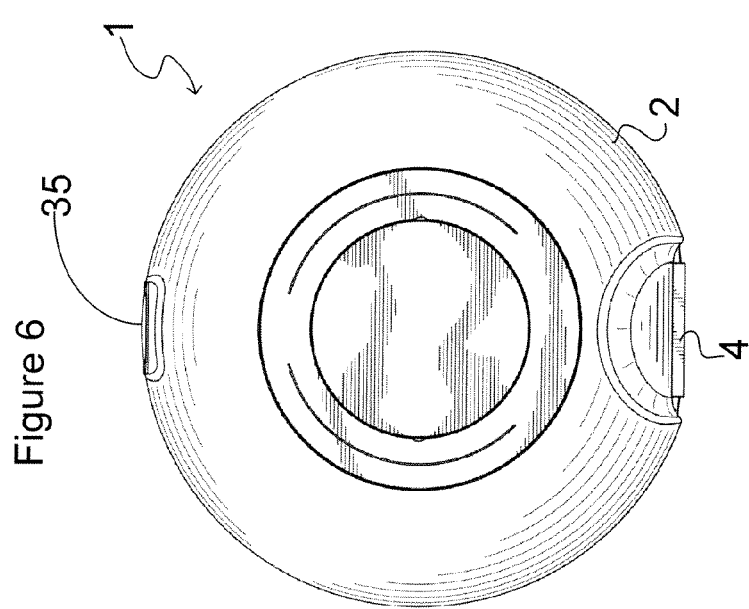
FIG. 6 is a top view of the device of FIG. 1.

FIGS. 1 to 7 show a skin measuring or monitoring device 1 according to one embodiment. The device includes a housing 2 that has a generally circular or elliptical cross-section, as shown in FIG. 6, and a substantially spherical shape, as shown in e.g. FIGS. 1 and 2. In this specification "substantially spherical shape" does not exclude the possibility of flat areas, such as the front face 6 of the device shown in the drawings, recessed areas around the camera lens etc. In the embodiment shown the substantially spherical housing 2 has a generally curved rear surface to fit a user's hand, while the front face 6 of the device is flat.

Figure 2:
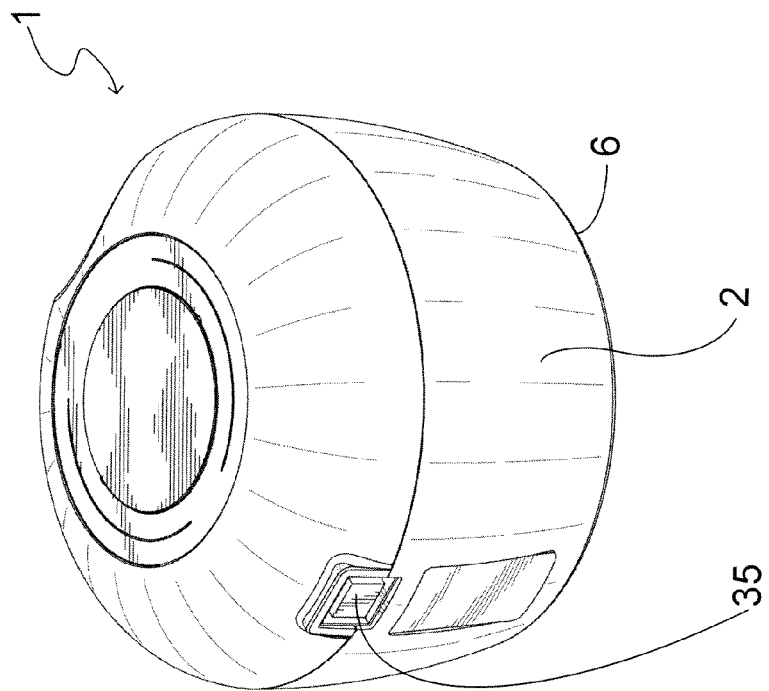
FIG. 2 is a second perspective view of the device of FIG. 1.
Figure 1:
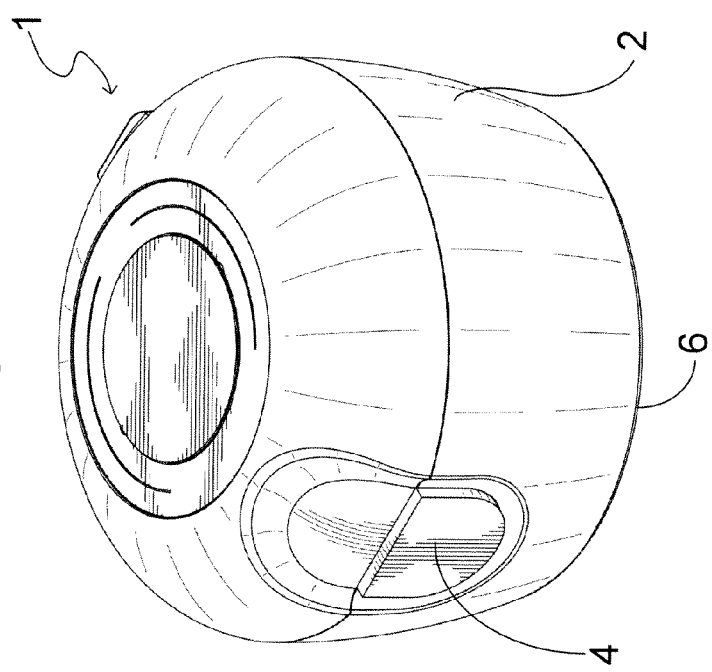
FIG. 1 is a perspective view of a handheld skin measuring or monitoring device according to one embodiment.
Figure 1A:
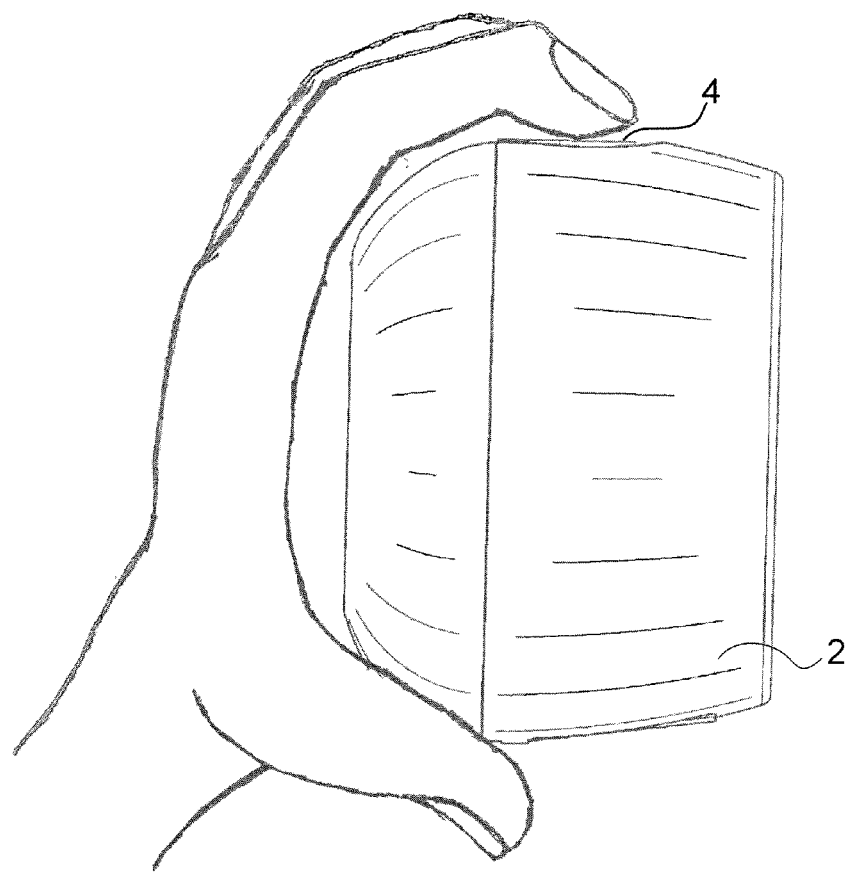
FIG. 1a shows the device of FIG. 1 in the cupped hand of a user.
Figure 5:
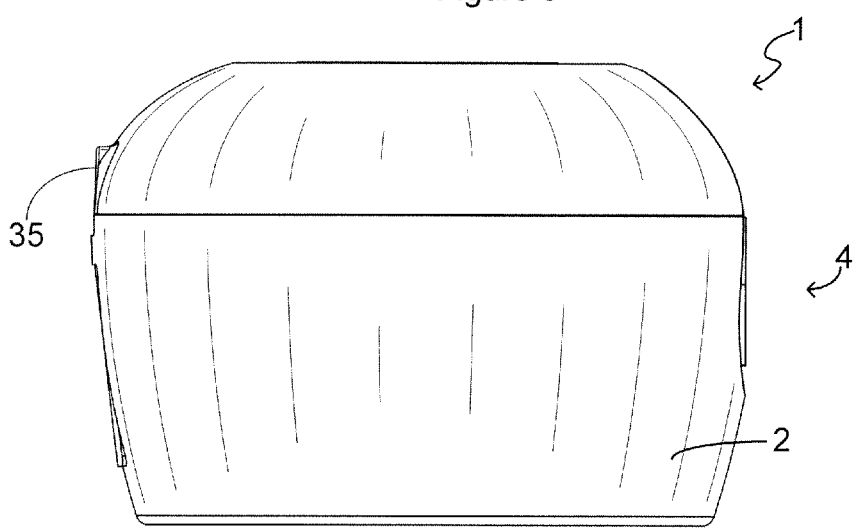
FIG. 5 is a third side view of the device of FIG. 1.

The housing 2 is made to be held in the cupped hand of a user, such that the user's fingers extend around the sides of the housing 2 and a user's finger or thumb (preferably the index or middle finger) can be positioned on capture button 4, as shown in FIG. 1a. This shape allows the device 1 to be positioned with a significant degree of flexibility. This is important because the device may be used to capture images for skin features in difficult to access areas, such as the underside of an immobile patient's leg. This is also useful where there is limited space available to access the skin feature. This shape also allows convenient one-handed operation, which in turn allows the user's other hand to be used to aid positioning of an immobile patient or for any other necessary purpose.

In one embodiment the housing 2 may have a diameter in the range around 85 to 115 mm (around 3.3 to 4.5 inches), preferably around 100 mm (around 3.9 inches). In the embodiment shown this diameter is measured transverse to the optical axis 7 (FIG. 3). This measurement provides a comfortable fit for most hand sizes. Parallel to the optical axis the housing 2 may measure around 70 mm (around 2.7 inches), this measurement being less than the diameter due to the flattened front face 6 of the device 1. The measurements of the housing are preferably sufficiently small to be comfortably held and sufficiently large that the average user's fingers and thumbs will not contact the optical apertures on the front surface, in the normal holding position shown in FIG. 1A.

The device 1 includes a camera 5 (FIG. 7) that may be mounted in the housing 2. The camera optical axis 7 extends forwards of the housing 2, as shown in FIG. 3.

The camera 5 may be mounted in fixed relation to a structured light arrangement 8, as shown in FIG. 8. The structured light arrangement 8 is configured to project three laser fan beams or stripes. The structured light arrangement 8 may include three laser fan-beam projectors 9 evenly distributed around the camera optical axis 7. In FIG. 8, the camera 5 and structured light arrangement 8 are mounted in a rigid framework 10. The laser fan-beam projectors 9 are preferably adjustably mounted to allow factory calibration of the structured light arrangement. For example, the laser fan-beam projectors 9 may be mounted using set-screws allowing small adjustments in the laser fan-beams.

Figure 7:
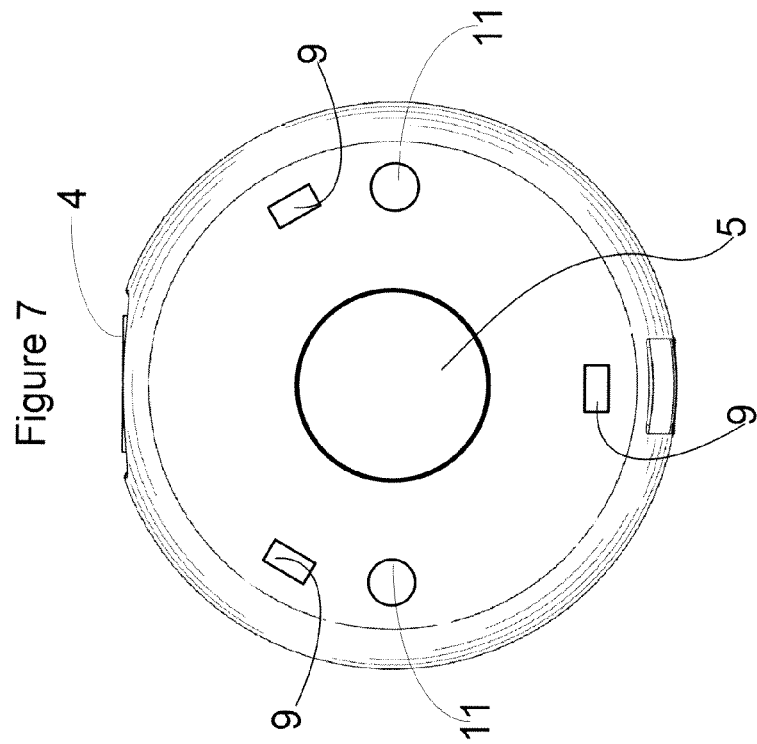
FIG. 7 is a cut-away top view of the device of FIG. 1.

FIG. 7 is a front view of the device 1 with the framework 10 omitted. The device may also include a transparent window, such that the camera and/or structured light arrangement is positioned behind the window. This figure shows the structured light projectors 9 and camera 5. In addition this figure shows a number of light sources 11. These light sources 11 may be used to illuminate the skin surface during some image capture steps, as will be described further below. These may be any suitable diffuse light sources for illumination of a skin surface. In one embodiment white light emitting diodes (LEDs) may be used.

A laser fan-beam emitted by a single laser fan-beam projector 9 is shown in FIG. 9. The laser fan-beam projector 9 is directed towards a surface S. The projected laser beam has a fan-beam angle $\propto$ and is relatively thin, such that a laser line 12 is projected onto a flat surface S. The shape of the fan-beam on a non-flat surface will be more complex, as will be discussed further below. The length of the laser fan-beam line 12 will depend on the fan-beam angle $\propto$, the distance between the laser fan-beam projector 9 and the surface S, and the relative angle between the laser fan-beam projector 9 and the surface S.

The laser fan-beam angle $\propto$ may be adjusted using an adjustable mask. For example, a small set screw may be positioned at each side of the projector 9. Adjustment of the two set-screws allows the fan-beam angle to be narrowed or broadened in the factory at the time of manufacturing or assembly.

The three laser fan-beams are arranged at an angle towards the optical axis. As shown in FIGS. 7 and 8 the laser fan-beam projectors 9 are mounted at a distance from the optical axis. This means that the three fan-beams will cross at a crossing point in front of the camera. This point may be on the optical axis. However, this will depend on the alignment of the camera and laser fan-beam projectors.

Figure 10:
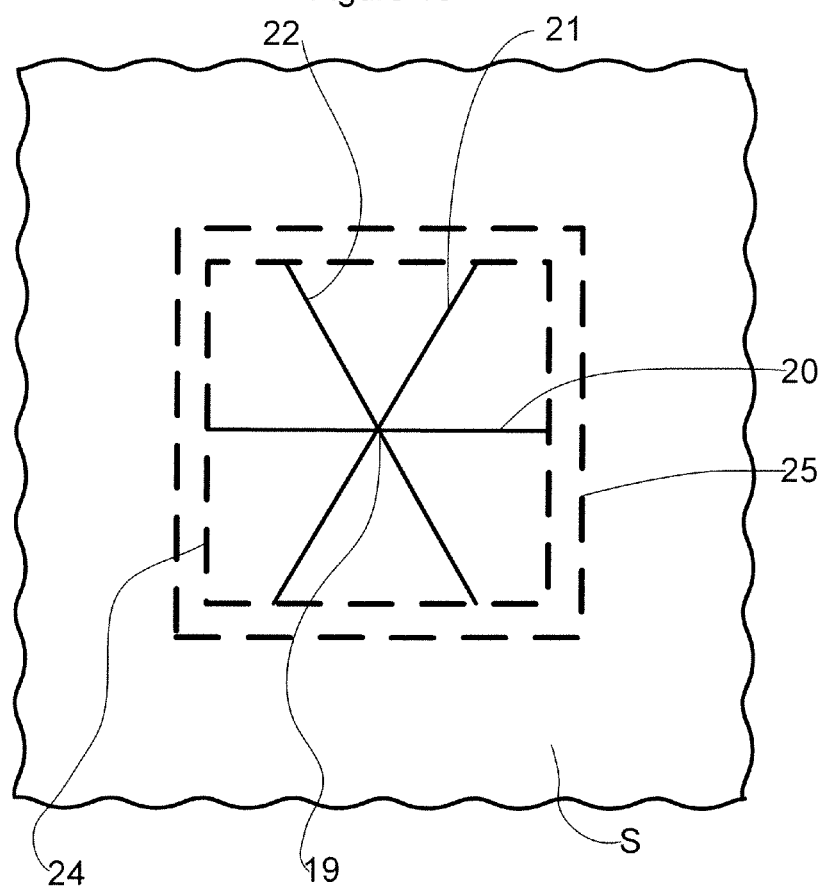
FIG. 10 shows a laser pattern projected onto a surface by the device of FIG. 1.
Figure 11:
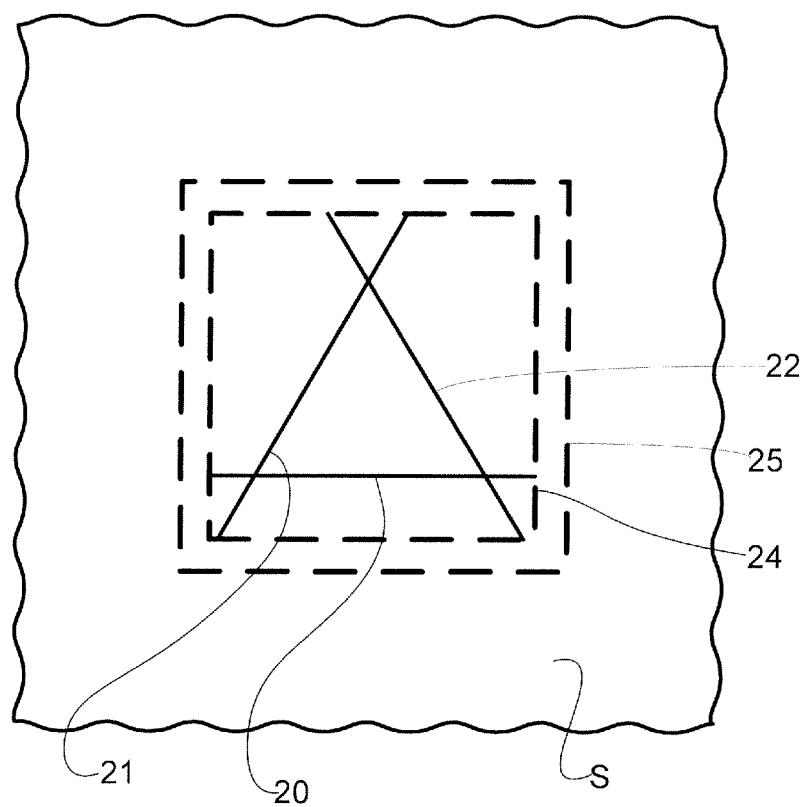
FIG. 11 shows a further laser pattern projected onto a surface by the device of FIG. 1.
Figure 12:
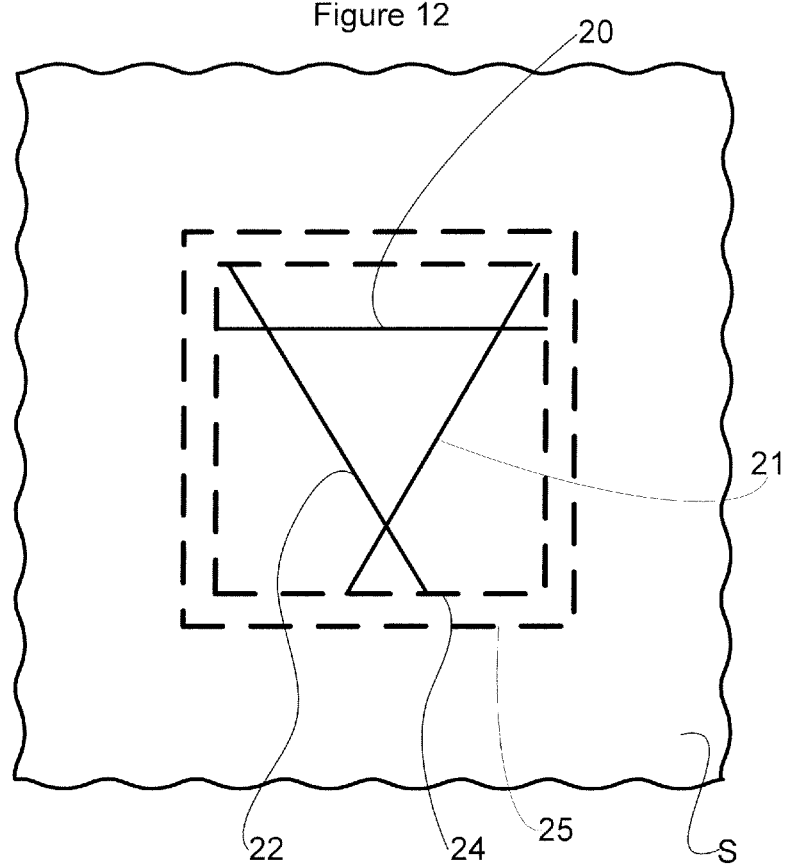
FIG. 12 shows a further laser pattern projected onto a surface by the device of FIG. 1.

FIG. 10 shows a laser pattern projected by the structured light arrangement onto a flat surface S. This pattern, and the patterns of FIGS. 11 and 12, are ideal patterns that are projected with the device perfectly perpendicular to the flat surface S. These patterns are included in order to illustrate the working of the device. In practical situations, making measurements on the skin surface, more complicated patterns will result.

Returning to FIG. 10, the flat surface S is arranged perpendicular to the camera optical axis and at the crossing point 19 of the three laser fan-beams 20, 21, 22. The crossing point may be at a distance in front of the device that corresponds to the mid-point of an optimum measurement range. The optimum measurement range may lie between optimum measurement limits, with the crossing point 19 at or near to the mid-point of those limits. The optimum measurement range may be a range in which acceptable focus and/or exposure are expected to be obtained. This will depend on the camera used.

This relationship between the crossing point 19 and the optimum measurement range provides convenient and intuitive user-positioning of the device 1. A user may simply position the device such that the crossing point 19 falls on the skin surface. In this embodiment the user is enabled, or guided, to align the device such that a predetermined pattern in the form of three stripes crossing at a point is seen on the skin. The user then knows that the device is at or near an optimum measurement distance, or within an optimum measurement range. There is no need for the user to look at some other alignment device such as a display screen on an attached computer. Alignment is possible using the light pattern itself.

In one embodiment the laser fan-beams are also arranged to mark out an image capture region. In FIG. 10 the laser fan-beams 20, 21, 22 have lengths such that their end points mark out a region indicated by dashed rectangle 24. Dashed rectangle 25 corresponds to the camera field of view. Dashed rectangles 24, 25 are not projected onto the surface, but are shown in the drawings to illustrate the working of the invention.

The position of the ends of the laser lines on the surface is governed by the laser fan-beam angles subtended by the lines and the distance between the device and the surface. The laser line position also depends on the angle of the fan-beam with respect to the optical axis.

This feature provides convenient and intuitive framing. A user can align the device such that the laser fan-beams 20, 21, 22 define a region 24 that includes a skin feature. Desirably the region will include some healthy skin around the skin feature. As this region 24 corresponds to the camera field of view 25, the images captured by the camera will be appropriately framed. Note that no viewfinder or display is required, and indeed in preferred embodiments the device is display-less. This has a number of advantages. A display-less device has a lower cost and lower power consumption than a device with a display.

Further, when measuring skin features in awkward places (e.g. on the underside of a leg that is being held up by the patient or an assistant) a display on the device is not always visible. However, the skin feature itself is usually visible. In some embodiments a remote display, connected by a wired or wireless connection, may be used. However, in preferred embodiments the device does not include a display, but uses the structured light elements themselves to assist in framing, for example as described above.

Preferably the region 24 is defined by the ends of the laser fan-beams, which span the region 24, passing through the inner part of region 24. This provides framing as discussed above, but also provides good sampling of structured light data from a central part of the image frame.

The region 24 preferably defines an area that corresponds to the camera frame area plus or minus 20%, more preferably plus or minus 15%. As the fan-beam is projected with a fan-beam angle ∝ (FIG. 9), this framing can be used over various ranges from the device to the skin surface. The correspondence of the region 24 to the frame 25 may vary with range while remaining within the above limits.

While the device may be positioned with the crossing point at the skin surface, as shown in FIG. 10, the device may also be used at other ranges. FIG. 11 shows the laser pattern on a flat surface S when the device is positioned closer to the surface S than in the position of FIG. 10. Here the three laser fan-beams 20, 21, 22 form an equilateral triangle and may extend beyond the triangle to define the region 24.

FIG. 12 shows the laser pattern on a flat surface S when the device is positioned further away from the surface S than in the position of FIG. 10. Here the three laser fan-beams 20, 21, 22 also form an equilateral triangle and may extend beyond the triangle to define the region 24. The triangle of FIG. 12 is inverted when compared to the triangle of FIG. 11.

Figure 13:
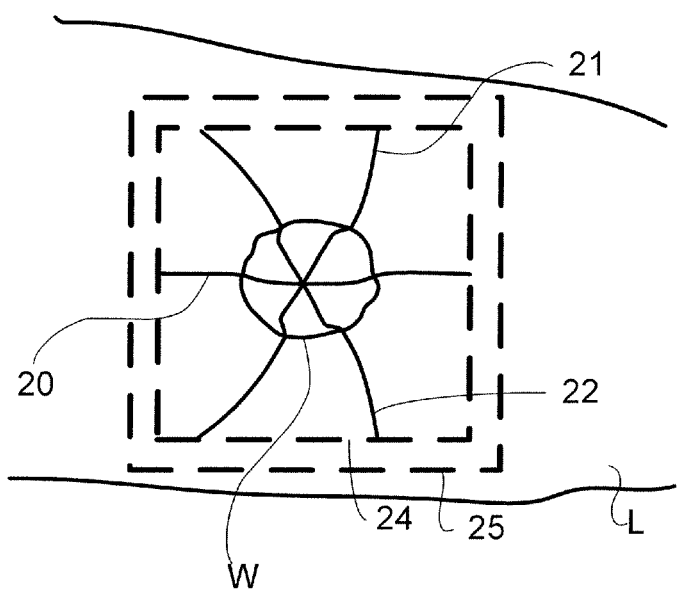
FIG. 13 shows a laser pattern projected onto a skin surface and skin feature by the device of FIG. 1.

FIG. 13 shows the laser pattern that may be projected onto a skin surface. In this example a patient has an ulcer or other wound W on his or her leg L. The leg L has a natural curvature from a high point along the centre and falling away towards the top and bottom of the image frame 25.

In addition, in this example the wound W is recessed in the skin surface. This is typical of ulcers, for example.

The laser fan-beam pattern reflects this more complex shape. Outside of the wound W the laser fan-beams form generally smooth curves. These curves contain data that reflect the overall shape of the patient's leg L.

Inside the wound W the laser-fan-beams will have a different curvature. Inside the wound W, the curves contain data that reflect the shape of the wound.

From the structured light data obtained from the three laser fan-beams, together with information about the wound boundary, it is possible to establish a model of the surface of the wound W and/or to obtain information such as a wound area, wound depth or wound volume. Various modeling techniques and measurements are discussed in the Applicant's copending application published as US2009/213213, the contents of which are hereby incorporated by reference herein. A model of the leg surface, or other anatomical surface as appropriate, may also be established if desired.

Figure 17:
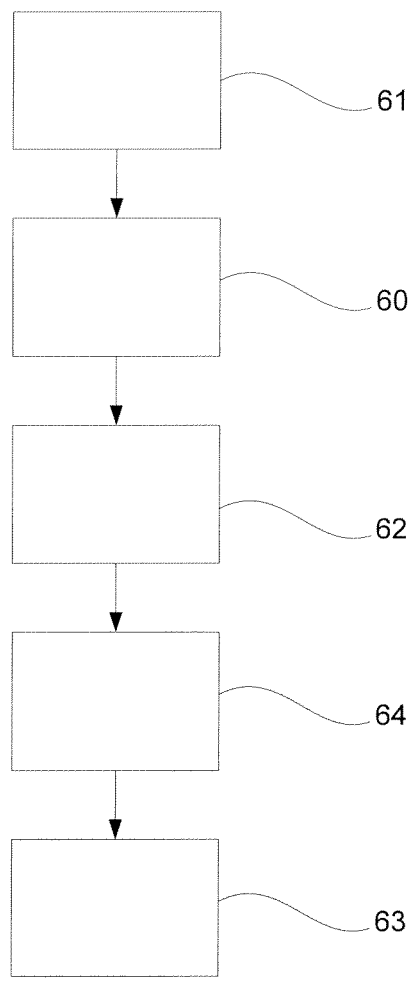
FIG. 17 is a flow diagram illustrating a data capture sequence.

The device 1 captures image data using the camera 5. One example of a capture sequence will now be described with reference to FIG. 17. Other sequences may also be suitable.

In a first step 60 a first image is captured without any laser fan-beams being switched on. This is an image of the skin surface and skin feature (e.g. wound, lesion, mole etc). Optionally this image capture may be preceded by one or more calibration images 61 designed to ensure that the first image is captured with acceptable exposure. The first image may be captured with illumination from the light sources 11, and exposure may be adjusted in the camera 5 or by adjusting the power output of the light sources 11. Alternatively the first image and its associated calibration images, if any, may be captured at a later point in the capture sequence.

In a second step 62 an image is captured with all three laser fan-beams turned on. This structured light image can be processed to obtain the structured light data allowing measurements to be made on the skin feature.

It is not always possible to differentiate unambiguously between the laser fan-beams in the structured light image. This may lead to errors or inaccuracies in any measurements that may be made. In order to address this problem, one or more disambiguation images may also be captured at step 63.

Preferably n−1 disambiguation images are captured, where n is the number of laser fan-beams used. Each image is captured with a subset of the laser fan-beams turned on. For example, each disambiguation image may include a single laser fan-beam. The data from the disambiguation images can then be used to identify the different laser fan-beams unambiguously in the structured light image.

As an alternative, a number of structured light images may be captured, each with just one laser fan-beam switched on. This avoids the need for disambiguation images, but could allow mis-registration due to movement between the structured light images.

The structured light images and/or disambiguation images may also be preceded by calibration images at step 64 to ensure correct exposure.

Preferably the images are captured over a very short space of time. This prevents significant movement between the images. In one embodiment, calibration images, the first image, structured light image and disambiguation images may all be captured in less than 1 second, preferably around 0.1-0.5 seconds. Memory, in particular a buffer, may be provided in the device 1 to allow rapid capture of image data. Data may be transferred at a slower rate from the handheld device 1 to an external device.

All images are preferably captured in response to a single user-actuation of the capture switch or button 4.

Thus, in use the device 1 may be directed by a user so that optical axis 7 is approximately aligned with the central region of wound W. The user may use the projected laser stripes to assist in framing, as discussed above. The laser fan-beams or stripes 20, 21, 22 are projected across wound W and the image or images are captured by camera 5. The skilled reader will understand that, due to the fixed angular relationship of the laser fan beams 20, 21, 22 and the optical axis 7 that the three dimensional positions of points along the laser fan beams may be determined from the structured light data. Models of the wound surface and the skin surface may then be developed to fit the three dimensional position data obtained.

The wound surface model and/or skin surface model may be an inelastic surface draped between the three-dimensional coordinates of the structured light elements, or an elastic surface stretched between the three-dimensional coordinates, or a model of the anatomy, or simply a scaled planar projection. A model of the anatomy may be a model retrieved from a library of models, or simply a geometric shape approximating anatomy (a cylinder approximating a leg, for example).

Figure 15:
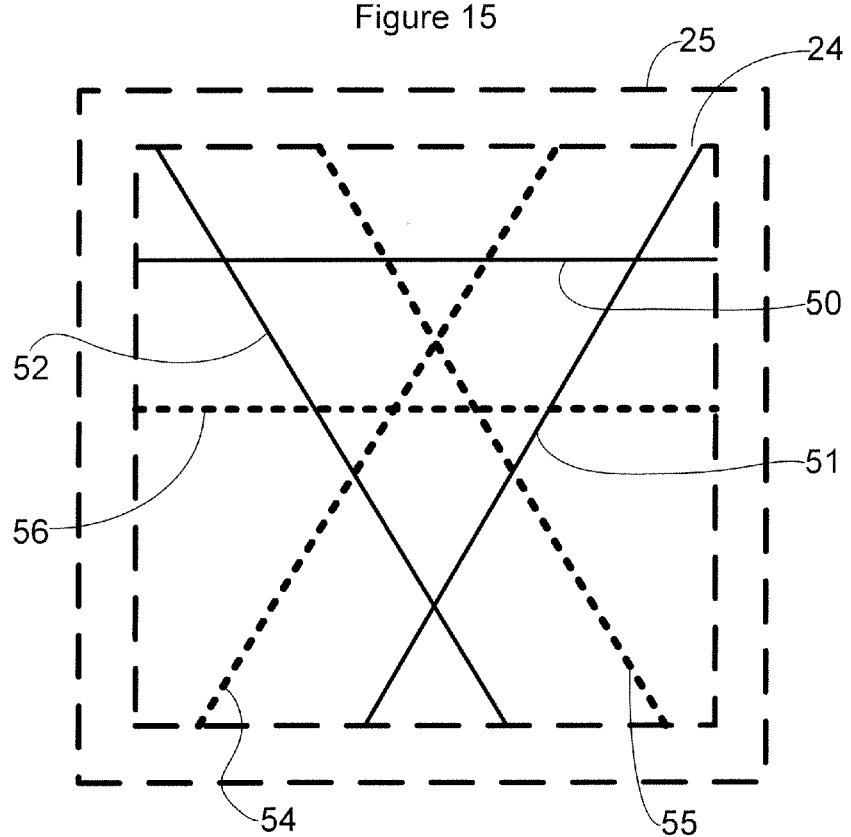
FIG. 15 shows a laser pattern projected onto a surface by a device according to a further embodiment.

FIG. 15 shows a laser pattern projected onto a surface by a device that is a modification of the device of FIG. 1. This device projects two sets of laser beams. In FIG. 15 one set of laser fan-beams 50, 51, 52 is shown in solid line, while a second set of laser fan-beams 54, 55, 56 is shown in dashed line. This is solely for the purposes of clarity. In practice the laser fan-beams may all be the same, or each set may be a different color or frequency.

In the embodiment of FIG. 15, the lasers are arranged such that a crossing point of the first set of laser fan-beams is a first distance from the device, and a crossing point of the second set of laser fan-beams is a second distance from the device. The first distance may correspond to a minimum measurement distance and the second distance to a maximum measurement distance (or the first and second distances are the limits of an optimum measurement range). A user adjusts the distance between the device and the skin such that the skin surface falls between the two crossing points.

Further, the position of the skin surface within the optimum measurement range may be apparent from the laser pattern. In FIG. 15 two triangles are defined by the two sets of laser fan-beams 50, 51, 52 and 54, 55, 56. If the device has two sets of laser projectors mounted together (i.e. two laser projectors at each point 9 in FIG. 7), then the triangles will be inverted with respect to each other (as is the case in FIG. 15) within the optimum measurement range. This is because of the inversion of each triangle with distance, as discussed above with reference to FIGS. 11 and 12. If the triangles are not inverted with respect to each other, then the skin surface is either closer than the nearer crossing point, or more distant than the further crossing point. In other words, when the user sees a predetermined pattern in the form of two triangles inverted with respect to each other, they know that the device is within the optimum measurement range.

Figure 16:
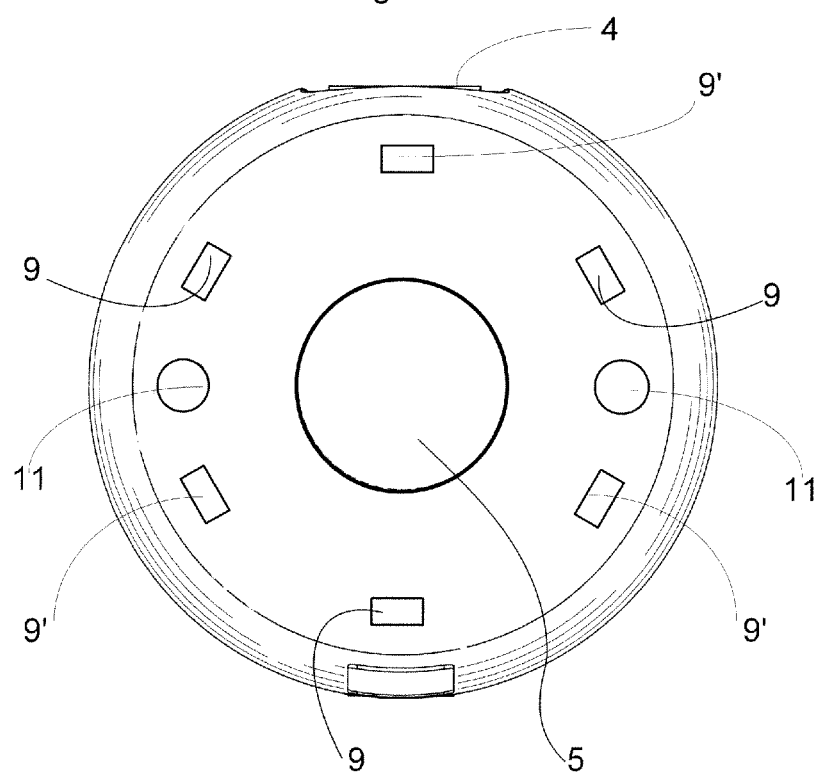
FIG. 16 shows a skin measuring or monitoring device according to a further embodiment.

In a further embodiment shown in FIG. 16, two sets of laser fan-beam projectors are offset, with a first set of projectors 9 positioned as in FIG. 7 and a second set of projectors 9' positioned in-between the projectors 9. In the embodiment of FIG. 16, each set is a set of three laser fan-beam projectors and the lasers are arranged such that a crossing point of the first set of laser fan-beams is a first distance from the device, and a crossing point of the second set of laser fan-beams is a second distance from the device. The first distance may correspond to a minimum measurement distance and the second distance to a maximum measurement distance (or the first and second distances are the limits of an optimum measurement range).

In this embodiment the triangles will be inverted when the skin surface is outside of the optimum measurement range. If the shapes of the two triangles are the same (i.e. not inverted) then the skin surface is within the optimum measurement range. In other words, when the user sees a predetermined pattern in the form of two triangles with the same orientation, they know that the device is within the optimum measurement range.

Figure 18:
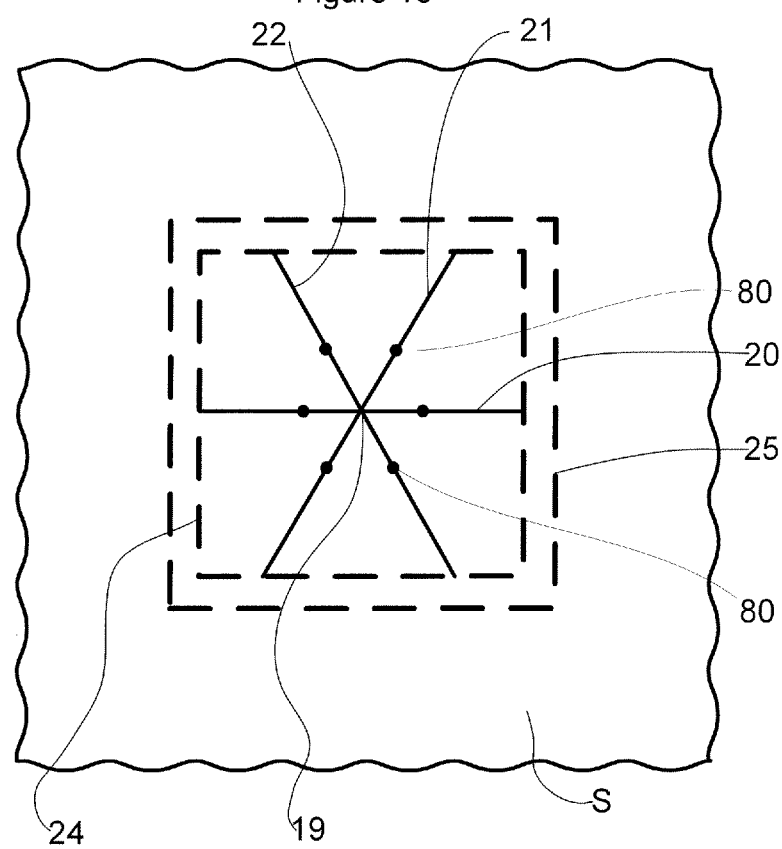
FIG. 18 shows a laser pattern projected onto a surface by a device according to yet a further embodiment.
Figure 19:
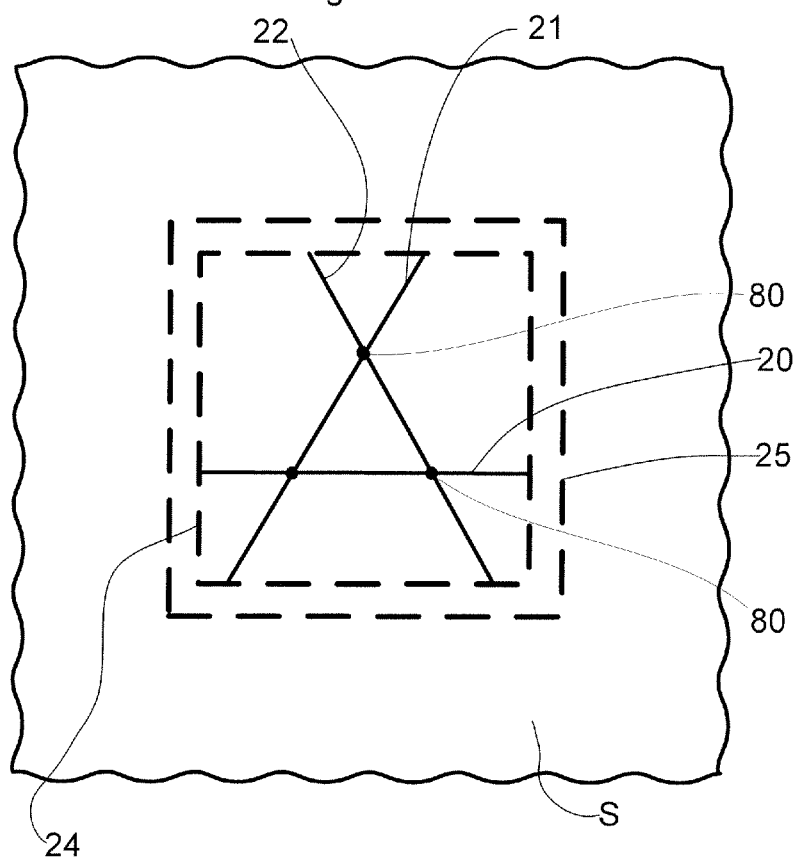
FIG. 19 shows a further laser pattern projected onto a surface by the device of the embodiment of FIG. 18.
Figure 20:
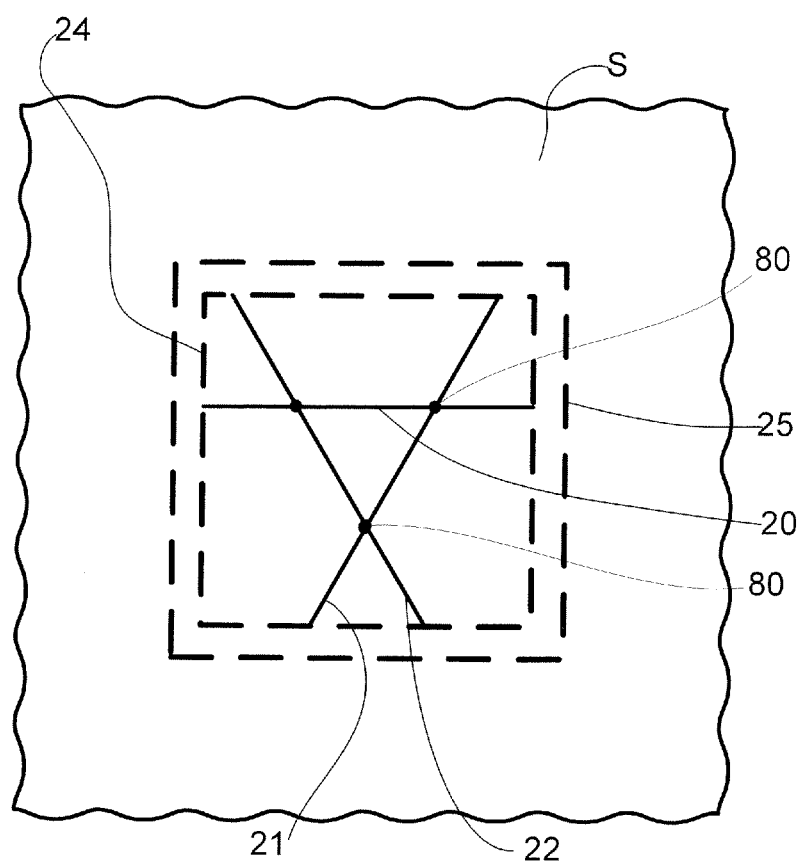
FIG. 20 shows a further laser pattern projected onto a surface by the device of the embodiment of FIG. 18.

In another embodiment shown in FIG. 18, a single set of three laser fan-beam projectors is provided, with the beams again arranged to cross in front of the device. In this embodiment the fan-beam angle ∝ and the angle with respect to the optical axis 7 are such that the three laser stripes cross at a crossing point 19 at an optimum measurement range. At other ranges the lines will form triangles. Further, the laser stripes of this embodiment may be projected together with small markers 80, such as laser spots or some other identifiable feature, such as dots, small lines crossing the laser stripe, small gaps in the laser stripe etc. The fan-beam angle and angle to the optical axis may be arranged such that when the markers 80 on different laser stripes align with each other, the device is at the outer limit of the optimum measurement range. Thus, FIG. 19 shows the laser pattern at the lower limit of the optimum measurement range, while FIG. 20 shows the laser pattern at an upper limit of the optimum measurement range. In this embodiment, when the user sees a predetermined pattern in the form of the lines crossing at a crossing point (as in FIG. 18) the user will know that the device is at or near an optimum measurement distance from the skin surface; or if the user sees a predetermined pattern in the form of a triangle, with markers 80 positioned outside the corners of the triangle the user will know that the device is within an optimum measurement range. If the markers 80 are inside the corners of the triangle then the device is outside the optimum measurement range. As with other embodiments, the equilateral triangle pattern is shown for illustrative purposes and corresponds to projection onto a flat surface perpendicular to the optical axis. More complex patterns result from projection onto more complex surfaces.

Figure 14:
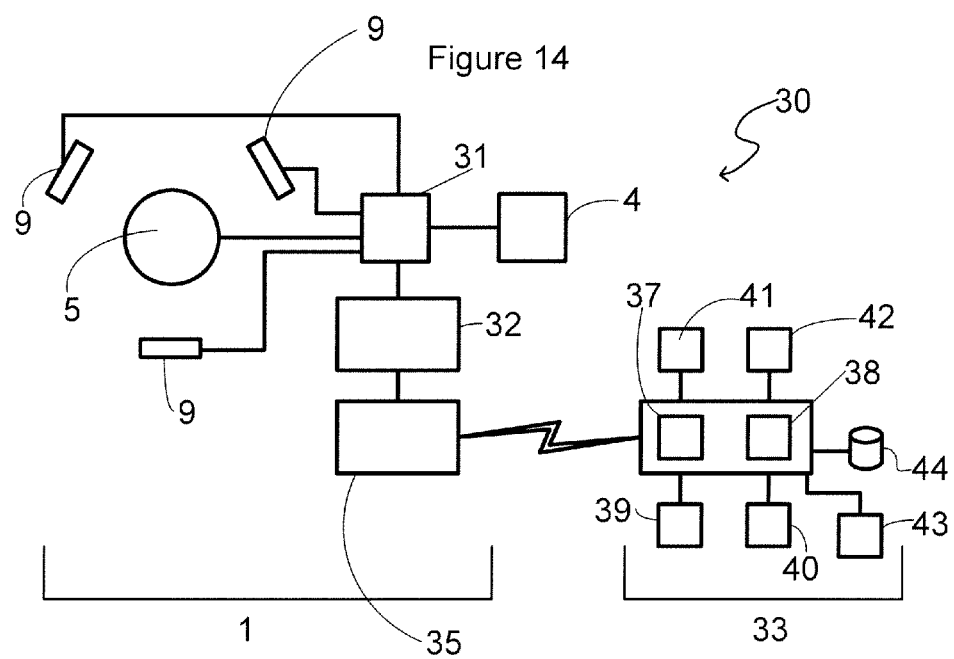
FIG. 14 shows a skin monitoring and measuring system according to one embodiment.

FIG. 14 shows the device 1 that may form part of a broader system 30. The device 1 includes a controller 31 that controls the camera 5, structured light projectors 9 and the light sources 11 (not shown in FIG. 14). The controller 31 is configured to control these components in response to user-actuation of the capture switch 4. The data generated by these devices is passed to a buffer memory 32, which holds the data until it can be passed from the device to an external computer 33.

The device 1 may be connected to the external computer by any suitable mechanism. Wired connections, such as USB or Firewire connections, may be used. The device may be configured to dock in a physical dock connected to the external computer 33. Alternatively, wireless connections may be used, including e.g. Bluetooth.

In any case, the device 1 includes a communications port 35 arranged for wired or wireless communications. In the embodiment shown in FIGS. 1 to 7 the communications port 35 is a USB port. Data is transmitted from the communications port 35 to the external computer 33.

The external computer 33 includes a processor 37 and memory 38. The external computer may also include a display 39 and output devices such as printers 40 and the like. The external computer 33 may include user input devices such as keyboard 41 and mouse 42. A stylus 43 may also be provided. The external computer 33 may be connected to a database 44.

The external computer may be any suitable computer or collection of computer devices, including: PDAs, Smartphones, Personal Computers, Laptops, Tablet computers etc.

Thus the device 1 is configured to capture data and transmit that data to the external computer 33. In one embodiment the device 1 does not perform any processing of the data, but simply passes it to the external computer 33. The device 1 preferably has no display. A user may capture data using the device 1 but analyses the data using the external computer 33.

Desirably a user may be permitted to manually define a skin feature boundary. This may be done using a mouse 42 or other pointing device, or the stylus 43. The boundary may be used to assist in developing a model of the wound surface and/or in determination of wound depth, area and/or volume. Utilizing manual input of the outline avoids the need for complex image processing capabilities. Further, this approach utilizes human image processing capabilities to determine the outline where automated approaches may be less effective.

Data may be maintained in the database 44 and used for monitoring of the skin feature over time. For example, records gathered over a time period can be used to monitor the healing of a wound or ulcer, or the growth of a potentially cancerous mole. Alerts may be generated if healing or growth exceeds a threshold.

The external computer may communicate with a central server that maintains the database 44. In this way data captured by a number of devices 1 may be centrally stored in a convenient manner.

This centralized system allows appropriate categorizing and storage of data for future use. For example, by mining historical data from the database it is possible to analyze the efficacy of a particular treatment or to compare different treatments. Statistical trends of conditions, treatments and outcomes can be monitored. This data can be used to suggest a particular treatment, based on a set of symptoms exhibited by a particular patient. Data can provide predictions for wound healing. Where actual healing differs from the prediction by more than a threshold, the system may issue an alert.

A healthcare provider may use the data to audit efficiency of its whole organization, departments within the organization or even individual workers. Historical data may be compared with historical worker schedules to determine whether workers are performing all tasks on their schedules. Efficiencies of different workers may be compared.

Data may be stored in a patient record along with measurement information (wound area, wound depth, wound volume etc). Where previous information has been stored comparative measurements may be made and an indication of improvement or deterioration may be provided. Data may be sent directly to a central database or distributed to medical professionals for evaluation. This allows an expert to review information obtained in the field and provide medical direction while the health practitioner is visiting the patient. The historic record allows patient progress to be tracked and re-evaluated, if necessary.

Measurements of other wound information may also be made. The color of the wound and the size (linear dimension, area or volume) of particular colored regions may also be calculated. These measurements may require a color reference target to be placed within the image capture area for accurate color comparison to be made.

There are thus provided methods of measuring wounds that are simple, inexpensive, repeatable and may be performed remotely, without contacting the skin surface. The methods may utilize human image processing capabilities to minimize the processing requirements. The methods do not require the placement of articles near the wound. The methods allow historical comparison of a wound. The device 1 is portable with relatively low processing requirements and enables records to be sent wirelessly or over a wired connection for evaluation and storage.

Further devices, such as GPS units, auxiliary sensors, temperature sensors, pH sensors, moisture sensors, odor sensors, optical probes, fluorescence probes and/or Doppler ultrasound probes, may be used in combination with the device 1, as discussed in the Applicant's copending application published as US2009/213213.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

The invention claimed is:

1. A handheld skin monitoring or measuring device, including:
   a camera having a camera optical axis; and
   a structured light arrangement configured to project three or more laser fan beams such that the laser fan beams cross at a crossing point in front of the camera and a user is enabled to position the handheld skin monitoring or measuring device at a distance from a skin surface within an optimum range without reference to a display by aligning the crossing point of the laser fan beams with the skin surface.

2. A handheld skin monitoring or measuring device as claimed in claim 1 wherein the structured light arrangement is configured to project the laser fan-beams such that a pattern formed by the laser fan beams on a skin surface varies with a distance between the device and the skin surface, and wherein the pattern is a predetermined pattern when the device is at a distance from the skin surface within an optimum range, such that a user is enabled to position the handheld skin monitoring or measuring device at a distance from the skin surface within the optimum range by adjusting the distance such that the predetermined laser pattern is formed on the surface.

3. A handheld skin monitoring or measuring device as claimed in claim 1 further including a capture switch, the device being arranged to capture data on actuation of the capture switch.

4. A handheld skin monitoring or measuring device as claimed in claim 1 further including a communications port, the device being configured to transmit data captured by the camera from the communications port.

5. A handheld skin monitoring or measuring device as claimed in claim 1 further including memory configured to store data captured by the camera.

6. A handheld skin monitoring or measuring device as claimed in claim 1, further including one or more light sources configured to illuminate the skin surface.

7. A handheld skin monitoring or measuring device as claimed in claim 1, configured to capture at least the following data in response to a single user capture instruction:
   an image with the laser fan beams switched off; and
   at least three images each including one or more laser fan beams, such that each laser fan beam is unambiguously identifiable.

8. A handheld skin monitoring or measuring device as claimed in claim 1, further including a substantially spherical housing dimensioned to fit a user's cupped hand, the camera and structured light arrangement being mounted in the housing.

9. A handheld skin monitoring or measuring device as claimed in claim 1, wherein the structured light arrangement is configured to project three laser fan beams from sources distributed evenly around the camera optical axis such that the three laser fan beams form a substantially equilateral triangle in any plane that is perpendicular to the camera optical axis and does not include the crossing point.

10. A handheld skin monitoring or measuring device as claimed in claim 1, wherein the structured light arrangement is configured to project three laser fan beams.

11. A handheld skin monitoring or measuring device, including:
    a camera having a camera optical axis; and
    a structured light arrangement configured to project three or more laser fan beams such that the laser fan beams cross at a crossing point in front of the camera, wherein the camera has a camera field of view and the three or more laser fan beams subtend fan beam angles corresponding to the camera field of view, such that the ends of the laser beams projected onto a skin surface define a region that substantially corresponds to an image frame of the camera.

12. A handheld skin monitoring or measuring device as claimed in claim 11 wherein the region occupies between 80% and 120% of the area of the image frame.

13. A handheld skin monitoring or measuring device, including:
    a camera having a camera optical axis and a camera field of view; and
    a structured light arrangement configured to project three or more laser fan beams such that the laser fan beams cross at a crossing point in front of the camera, the laser fan beams subtending fan beam angles corresponding to the camera field of view, such that the ends of the laser beams projected onto a skin surface define a region that substantially corresponds to an image frame of the camera.

14. A handheld skin monitoring or measuring device as claimed in claim 13 wherein the region occupies between 80% and 120% of the area of the image frame.

15. A handheld skin monitoring or measuring device as claimed in claim 13, wherein the structured light arrangement is configured to project three laser fan beams from sources distributed evenly around the camera optical axis such that the three laser fan beams form a substantially equilateral triangle in any plane that is perpendicular to the camera optical axis and does not include the crossing point.

16. A method of capturing data concerning a skin feature using a handheld skin monitoring or measuring device, including: a camera having a camera optical axis and a camera field of view; a structured light arrangement configured to project three or more laser fan beams such that the laser fan beams cross at a crossing point in front of the camera; the laser fan beams subtending fan beam angles corresponding to the camera field of view, such that the laser beams projected onto a skin surface define a region that substantially corresponds to an image frame of the camera; the method including:

directing the handheld skin monitoring or measuring device towards a skin surface;

projecting at least some of the laser fan beams using the structured light arrangement; and adjusting a position of the handheld skin monitoring or measuring device such that laser fan beams define a desired image region on the skin surface; and capturing data using the camera.

17. A display-less handheld skin monitoring or measuring device including:

a substantially spherical housing dimensioned to fit the cupped hand of a user;

a camera mounted in the housing;

a structured light arrangement mounted in the housing and configured to project three or more laser fan beams such that the laser fan beams cross at a crossing point in front of the camera; and a communications link configured to transmit image data captured by the camera.

18. A display-less handheld skin monitoring or measuring device as claimed in claim 17, including a capture button positioned on the substantially spherical housing such that, in use, the capture button is accessible to one of the user's fingers or thumb.

* * * * *

UNITED STATES PATENT AND TRADEMARK OFFICE
CERTIFICATE OF CORRECTION

PATENT NO. : 9,179,844 B2
APPLICATION NO. : 13/686738
DATED : November 10, 2015
INVENTOR(S) : Fright et al.

Page 1 of 2

It is certified that error appears in the above-identified patent and that said Letters Patent is hereby corrected as shown below:

Title Page

On Page 2, in item (56), under References Cited, under Other Publications, under the reference of Ahroni, JH, line 2, please delete "CLinical" and insert -- Clinical --

On Page 2, in item (56), under References Cited, under Other Publications, under the reference of Brown, G., line 1, please delete "uncle" and insert -- ulcer --

On Page 2, in item (56), under References Cited, under Other Publications, under the 2nd reference of Fitzpatrick, R., et al., line 2, please delete "(Executivev Summary)" and insert -- (Executive Summary) --

On Page 3, in item (56), under References Cited, under Other Publications, under the 1st reference of Salcido, R., et al., line 1, please delete "WOund" and insert -- Wound --

On Page 3, in item (56), under References Cited, under Other Publications, under the reference of Sani-Kick, S., et al., lines 1-2, please delete "Recording and trasmission of digital wound images with the hep of a mobile device" and insert -- Recording and transmission of digital wound images with the help of a mobile device --

On Page 4, in item (56), under References Cited, under Other Publications, under the reference of Wang, Y., et al., lines 1-3, please delete "A comparison o digital planimetry and transparency tracing based methods for measuring diabetic cutaneoud ulcer surface area" and insert -- A comparison of digital planimetry and transparency tracing based methods for measuring diabetic cutaneous ulcer surface area --

On Page 4, in item (56), under References Cited, under Other Publications, under the reference of Wild, T., et al., line 2, please delete "POster" and insert -- Poster --

Signed and Sealed this
Twenty-third Day of August, 2016

Michelle K. Lee
*Director of the United States Patent and Trademark Office*

On Page 4, in item (56), under References Cited, under Other Publications, under the 1st reference of Woodbury, et al., line 2, please delete "measurement toolq" and insert -- measurement tool --

On Page 4, in item (56), under References Cited, under Other Publications, under the 2nd reference of Woodbury, et al., line 1, please delete "Pressur" and insert -- Pressure --